United States Patent [19]

Arraudeau et al.

[11] Patent Number: 4,820,510

[45] Date of Patent: * Apr. 11, 1989

[54] COSMETIC MAKE-UP COMPOSITION

[75] Inventors: Jean-Pierre Arraudeau; Jeanne Patraud, both of Paris; Louis Le Gall, Bures S/Yvette, all of France

[73] Assignee: L'Oreal, Paris, France

[*] Notice: The portion of the term of this patent subsequent to Apr. 21, 2004 has been disclaimed.

[21] Appl. No.: 40,667

[22] Filed: Apr. 21, 1987

Related U.S. Application Data

[63] Continuation-in-part of Ser. No. 909,725, Sep. 22, 1986, abandoned, which is a continuation of Ser. No. 540,752, Oct. 11, 1983, Pat. No. 4,659,562.

[30] Foreign Application Priority Data

Oct. 12, 1982 [FR] France ................................ 82 17051

[51] Int. Cl.$^4$ .............................................. A61K 7/021
[52] U.S. Cl. ........................................ 424/63; 424/64; 424/69
[58] Field of Search ........................................... 424/63

[56] References Cited

U.S. PATENT DOCUMENTS 3,266,995  8/1966  Lanzet et al. ......................... 424/63
4,119,712 10/1978  Goldner et al. ....................... 424/63
4,659,562  4/1987  Arraudeau et al. ................... 424/63

FOREIGN PATENT DOCUMENTS 2002652  2/1979  United Kingdom ................. 424/63

Primary Examiner—Sam Rosen
Attorney, Agent, or Firm—Cushman, Darby & Cushman

[57] ABSTRACT

A cosmetic make-up composition comprises, in combination, cosmetic make-up components and, as a binding agent therefor, an intimate mixture of from 5 to 95 percent by weight of said mixture of finely divided silica and about 95 to about 5 percent by weight of said mixture of finely divided polyethylene fibers having a fibrillar structure.

13 Claims, No Drawings

COSMETIC MAKE-UP COMPOSITION

This application is a continuation-in-part of application Ser. No. 06/909,725, filed Sept. 22, 1986, now abandoned, which is a continuation of application Ser. No. 06/540,752, filed Oct. 11, 1983, now U.S. Pat. No. 4,659,562.

The present invention relates to a cosmetic facial make-up composition.

Cosmetic make-up compositions for the face such as eyelid shadow or liner, cheek rouge, anti-circle or cover formulations, lipsticks and the like improve facial esthetics by imparting more relief to the face, eyes and lips and by intensifying their color.

These compositions can be provided in aqueous or anhydrous form in colors suitable to the individual user and they are applied to the surface of the skin of the eyelids or the lips.

One disadvantage encountered most frequently during the use of cheek rouge and eyelid shadow reside in the fact that after a certain lapse of time, the composition, due to wrinkling of the skin and the eyelids, has a tendency to lose its uniformity and to concentrate more or less rapidly and deeply in the folds of the skin. It results from it an effect considered generally unaesthetic.

Despite numerous investigations in this area, it has not heretofore been possible to perfect make-up products capable of maintaining their uniformity during more or less prolonged periods of time, that is to say, having properties commonly termed "creaseproof".

The present invention provides a very satisfactory solution to this problem by using a novel binding agent in cosmetic make-up composition.

The studies that have been carried out have, in effect, shown that the make-up compositions containing this binding agent do not cause the formation of unaesthetic folds; they prevent the migration of the make-up, and they do not require, consequently, new or repeated applications as is most often the case with conventional make-up compositions.

The present invention thus relates to a cosmetic make-up composition containing as the binding agent, an intimate mixture of 5 to about 95 weight percent of said mixture of finely divided silica and about 95 to about 5 weight percent of said mixture of finely divided polyethylene fibers having a fibrillar structure.

The binding agent of the make-up compositions of the present invention is preferably obtained by the pulverization by fluid energy of silica and polyethylene, for example with the aid of a micronizer.

The co-pulverization of polyethylene fibers and silica reduces the particle size of the silica, defibrillates the polyethylene fibers and produces an intimate mixture, the polyethylene fibers and the silica particles being maintained together and not being able to be separated by conventional mechanical means.

The polyethylene of this intimate mixture has a molecular weight greater than about 400,000, a softening point in the order of 120°-130° C. and a melting point in the order of 130 to about 135° C. The finely divided polyethylene contains an amount greater than about 90 weight percent of fibers having an average length in the order of about 10μ and a diameter lower than about 1μ. Preferably the polyolefin fibers are very fibrillar and have a very high specific area, generally between 5 and 15m$^2$/g.

The silica is preferably a silica aerogel (synthetic amorphous silica) having an average particle diameter in the order of 2 to about 10μ, a surface area in the order of 300 to about 400m$^2$/g, a pore volume of at least about 1.2cm$^3$/g and an average pore diameter in the order of 150 to about 250A.

In accordance with a particular embodiment of the present invention this intimate mixture contains between about 45 and about 75% and preferably between 50 to 60% by weight of silica aerogel having an average diameter in order of 2 to about 10μ, and between about 55 and 25% and preferably between 40 and 50% by weight of finely divided polyethylene fibers having a specific area between 5 and 15m$^2$/g.

The binding agent of the cosmetic make-up compositions according to the present invention, such as defined above, can be one of those described in French Pat. No. 81.03535 and is principally a product sold by W. R. Grace & Co. under the tradename "SP5-1776" (60% amorphous silica—40% low density polyethylene having a specific area of 6 to 10m$^2$/g) or "SP5-2076" (50% amorphous silica—50% low density polyethylene having a specific area of 6 to 10m$^2$/g).

The binding agent is generally present in an amount between 0.5 and 20 percent by weight of the composition of the present invention.

The make-up composition in accordance with the present invention can be provided in anhydrous or aqueous form. In this latter case the composition is generally an emulsion of the oil-in-water or water-in-oil type or a suspension.

When the make-up composition of the present invention is provided in anhydrous form, the composition is generally a product containing a fatty body and optionally one or more organic solvents.

When the make-up composition according to the invention is provided in anhydrous fatty form, it comprises, generally 0.5 to 20 weight percent binding agent, 5 to 98 weight percent of a fatty body, 0,5 to 40 weight percent and preferably 1 to 30 weight percent of a mineral or organic charge, 0 to 80 weight percent of a solvent and 0 to 30 weight percent and preferably 1 to 25 weight percent of one or more colored pigments.

The mineral or organic charges of the above anhydrous compositions are preferably talc, rice starch, wheat starch, corn starch, oat or wheat germ powder and kaolin.

The fatty body is at least one oil or a mixture of at least one oil and at least one wax.

Representative oils usefully employed in accordance with the present invention include:

mineral oils such as paraffin oil, petrolatum oil and mineral oils having a boiling point between 310° and 410° C., oils of animal origin such as Purcellin oil, perhydrosqualene and calophyllum oil, vegetable oils such as sweet almond oil, palm oil, avocado oil, olive oil, ricin oil, the oil of cereal germs such as the oil of wheat germ, silicone oils such as dimethyl polysiloxane synthetic esters such as butyl myristate, isopropyl myristate, cetyl myristate, isopropyl palmitate, butyl stearate, hexadecyl stearate, isopropyl stearate, octyl stearate, isocetyl stearate, decyl oleate, hexyl laurate, propylene glycol dicaprylate, and diisopropyl adipate, organic alcohols such as oleyl alcohol, linoleic alcohol, linolenic alcohol, isostearyl alcohol and octyl dodecanol, esters derived from lanolic acid such as isopropyl lanolate and isocetyl lanolate, as well as other oils, such as acetyl glycerides, the octanoates and decanoates of alcohols and polyalcohols such as those of glycol and glycerol, the ricinoleates of alcohols and polyalcohols such as that of cetyl.

Representative waxes usefully employed in accordance with the present invention include mineral waxes such as microcrystalline waxes, paraffin wax and petrolatum wax, fossil waxes such as ozokerite and montan wax, waxes of animal origin such as beeswax, spermaceti wax, lanolin wax, derivatives proceeding from lanolin such as lanolin alcohols, hydrogenated lanolin, hydroxylated lanolin, acetylated lanolin, lanolin fatty acids and the alcohol of acetylated lanolin, waxes of vegetable origin such as candellila wax, Carnauba wax, Japan wax and cocoa butter, hydrogenated oils which are solid at 25° C. such as hydrogenated ricin oil, hydrogenated palm oil, hydrogenated tallow and hydrogenated coconut oil, synthetic waxes such as polyethylene waxes, copolymerized polyethylene waxes, fatty esters which are solid at 25° C. such as propylene glycol monomyristate and myristyl myristate, silicone waxes such as methyloctadecaneoxypolysiloxane and poly(dimethylsiloxy)stearyloxysiloxane, as well as other waxes such as cetyl alcohol, stearyl alcohol, mono-, di- and triglycerides solid at 25° C., stearyl monoethanolamide, rosin and its derivatives such as glycol and glycerol abietates, sucro glycerides and the oleates, myristates, lanolates, stearates and dihydroxy stearates of calcium, magnesium, zinc and aluminum.

Representative solvents usefully employed in the present invention include isoparaffins, linear or cyclic silicones having a boiling point lower than 200° C., chlorinated solvents and the like.

Representative colored pigments usefully employed in the present invention include carbon black or black iron oxide, chromium oxides, yellow, brown and red iron oxides, the ultramarines (polysulfides of aluminosilicates) manganese pyrophosphate, ferric blue, titanium dioxide as well as certain metallic powders such as those of silver of aluminum. The pigments are most often used in admixture with nacreous agents such as bismuth oxychloride, mica-titanium and guanine crystals, as well as with certain organic dyes, such as carmine and organic lakes.

Moreover, the cosmetic make-up compositions of the present invention can also contain anti-oxidant agents, such as the propyl, octyl and dodecyl esters of gallic acid, butyl hydroxy anisole, butyl hydroxy toluene and nordihydroguaiaretic acid, as well as perfumes, preservatives or thickening agents, such as cellulose derivatives, xanthene gums, guar gums, carob bean gums, alginates and carreghenates, silicate complexes and organically modified clays.

When the cosmetic make-up of the present invention is provided in the form of a water-in-oil emulsion, this emulsion comprises 5 to 80 weight percent of a water phase, 1 to 40 weight percent of an oil phase, 2 to 15 weight percent of an emulsifying agent 0.5 to 20 weight percent of the binding agent as defined above 0.5 to 40 weight percent and preferably 1 to 30 weight percent of a mineral or organic charge, 0 to 20 weight percent of a thickening agent and 0 to 30 weight percent and preferably 1 to 25 weight percent of at least one colored pigment.

When the cosmetic make-up of the present invention is provided in the form of a water-in-oil emulsion, this emulsion comprises 1 to 96.5 weight percent of a water phase, 1 to 30 weight percent of an oil phase, 1 to 15 weight percent of an emulsifying agent, 0.5 to 20 weight percent of the binding agent as defined above, 0,5 to 40 weight percent and preferably 1 to 30 weight percent of a mineral or organic charge, 0 to 20 weight percent of a thickening agent and 0 to 30 weight percent and preferably 1 to 25 weight percent of at least one colored pigment.

The oil phase of these emulsions can comprise at least one oil such as those enumerated above, optionally in admixture with at least one wax, also as listed above.

Representative emulsifying agents usefully employed in these emulsions include, particularly, anionic surfactants and more particularly soaps of amines or salts of lanolic acid, as well as anionic surfactants and the like.

The mineral or organic charges as well as the colored pigments employed in these emulsions can be the same as those mentioned above with respect to the anhydrous compositions.

The cosmetic make-up compositions in accordance with the present invention can also contain various components such as sterols, lecithins, polyalcohols, anti-oxidant agents, perfumes, preservatives, as well as certain active products.

Representative active compounds or agents include, principally, keratolytic agents, anti-inflammatory agents, cicatrisive agents, benzyl peroxide, salicylic acid, retinoic acid, collagen and the like.

The following non-limiting examples are given to illustrate the cosmetic make-up compositions in accordance with the present invention.

| Example 1 - Anhydrous eyelid make-up | |
|---|---|
| Bees wax | 15 g |
| Petrolatum | 5 g |
| Hydrogenated ricin oil | 5 g |
| Polyethylene wax | 10 g |
| Isoparaffin | 44.8 g |
| Propyl parahydroxybenzoate | 0.2 g |
| Talc | 5 g |
| Binding agent - "SP5-1776" | 2 g |
| Mica-titanium | |
| Titanium dioxide | 13 g |
| Iron oxide | |
| | 100 g |
| Example 2 - Anhydrous facial camouflage | |
| Candellila wax | 4 g |
| Microcrystalline wax | 8 g |
| Cocoa butter | 8 g |
| Isopropyl myristate | 44.9 g |
| Talc | 7 g |
| Butyl hydroxy toluene | 0.1 g |
| Iron oxides | 5 g |
| Titanium dioxide | 20 g |
| Binding agent - "SP5-2076" | 3 g |
| Example 3 - Lipstick | |
| Beeswax | 8 g |
| Ethylene glycol dicaprylate | 16.5 g |
| Paraffin | 3 g |
| Carnauba wax | 5 g |
| Trilaurin | 10 g |
| Hydrogenated ricin oil | 5 g |
| Butyl hydroxy toluene | 0.1 g |
| Lanolin | 1 g |
| Kaolin | 5 g |
| Modified starch | 5 g |
| Binding agent - "SP5-1776" | 1 g |
| Isoparaffin | 40.4 g |

| Example 4 - Lipstick | |
|---|---|
| | 100.0 g |
| Beeswax | 15 g |
| Petrolatum | 12 g |
| Polyethylene wax | 10 g |
| Trilaurin | 10 g |
| Hydrogenated ricin oil | 3 g |
| Liquid lanolin | 9 g |
| Butyl hydroxy toluene | 0.1 g |
| Micronized talc | 3 g |
| Modified starch | 5 g |
| Binding agent - "SP5-1776" | 0.5 g |
| Volatile silicone | 32.4 g |

The lipsticks of the Examples 3 and 4, applied prior to the application of a lip rouge, prevent the migration of the rouge on the edges of the lips and thus assure a long lasting sharp outline of the lips.

| Example 5 - Anhydrous eyelid make-up | |
|---|---|
| Beeswax | 12 g |
| Petrolatum | 5 g |
| Carnauba wax | 3 g |
| Hydrogenated ricin oil | 5 g |
| Polyethylene wax | 10 g |
| Isoparaffin | 44.8 g |
| Propyl parahydroxybenzoate | 0.2 g |
| Talc | 5 g |
| Binding agent "SP5-1776" | 2 g |
| Mica-titanium | 6 g |
| Titanium dioxide | 2 g |
| Iron oxide | 5 g |

| Example 6 - Mascara in the form of an oil-in-water emulsion | |
|---|---|
| Stearic acid | 2.5 g |
| Polyethoxylated sorbitan monostearate | 0.5 g |
| Petrolatum oil | 3 g |
| Petrolatum | 5 g |
| Triethanolamine | 1 g |
| Carnauba wax | 2 g |
| Bees wax | 7 g |
| Talc | 3 g |
| Black iron oxide | 5 g |
| Imidazolidinyl urea | 0.3 g |
| Binding agent "SP5-1776" | 1 g |
| Sterile, permuted water, amount sufficient for | 100 g |

| Example 7 - Cheek make-up in the form of a water-in-oil emulsion | |
|---|---|
| Magnesium lanolate | 4 g |
| Hydrogenated lanolin | 13 g |
| Paraffin oil | 8 g |
| Microcrystalline wax | 4.5 g |
| Ozokerite | 3 g |
| Carnauba wax | 5 g |
| Glycerides of saturated fatty acids | 4.5 g |
| Methyl parahydroxybenzoate | 0.3 g |
| Iron oxides | 3.5 g |
| Corn starch | 5 g |
| Mica-titanium | 3 g |
| Binding agent "SP5-1776" | 0.5 g |
| Sterile permutted water, amount sufficient for | 100 g |

| Example 8 - Eyelid make-up in the form of an oil-in-water | |
|---|---|
| Petrolatum oil | 12 g |
| Bees wax | 10 g |
| Carnauba wax | 7 g |
| Sodium borate | 1 g |
| Propyl parahydroxybenzoate | 0.15 g |
| Imidazolidinyl urea | 0.30 g |
| Iron oxides | 5 g |
| Corn starch | 7 g |
| Mica-titanium | 3 g |
| Binding agent "SP5-1776" | 2.5 g |
| Sterile permutted water, amount sufficient for | 100 g |

| Example 9 - Anhydrous cheek make-up | |
|---|---|
| Paraffin oil | 45 g |
| Petrolatum | 12 g |
| Carnauba wax | 20 g |
| Ozokerite | 3 g |
| Propyl parahydroxybenzoate | 0.1 g |
| Butyl hydroxy toluene | 0.05 g |
| DC red 7 | 0.2 g |
| Iron oxides | 2 g |
| Talc | 3 g |
| Corn starch | 0.5 g |
| Binding agent "SP5-1776" | 2 g |
| Mica-titanium | 12.15 g |

| Example 10 - Anti-circle formulation in the form of a water-in-oil emulsion | |
|---|---|
| Ester of sorbitan and fatty acid | 7 g |
| Isopropyl myristate | 12 g |
| Bees wax | 4 g |
| Carnauba wax | 3 g |
| Imidazolidinyl urea | 0.3 g |
| Methyl parahydroxybenzoate | 0.1 g |
| Iron oxides | 6.9 g |
| Talc | 5 g |
| Titanium dioxide | 2 g |
| Binding agent "SP5-1776" | 1 g |
| Sterile, permutted water, amount sufficient for | 100 g |

| Example 11 - Cheek make-up in the form of a water-in-oil emulsion | |
|---|---|
| Magnesium lanolate | 4 g |
| Paraffin oil | 8 g |
| Microcrystalline wax | 4.5 g |
| Carnauba wax | 5 g |
| Glycerides of saturated fatty acids | 4.5 g |
| Methyl parahydroxybenzoate | 0.3 g |
| Talc | 30 g |
| Binding agent "SP5-1776" | 0.5 g |
| Seerile permutted water, amount sufficient for | 100 g |

| Example 12 - Mascara in the form of an oil-in-water emulsion | |
|---|---|
| Stearic acid | 3 g |
| Carnauba wax | 2 g |
| Paraffin wax | 1 g |
| Petrolatum oil | 3 g |
| Ozokerite | 8 g |
| Corn starch | 1 g |
| Imidazolidinyl urea | 0.3 g |
| Binding agent "SP5-1776" | 1 g |
| Triethanolamine | 2 g |
| Sterile permutted water, amount sufficient for | 100 g |

| Example 13 - Anhydrous anti-circle | |
|---|---|
| Bees wax | 5 g |
| Paraffin wax | 4,75 g |
| Paraffin oil | 41 g |
| Microcrystalline wax | 4 g |
| Propyl parahydroxybenzoate | 0.2 g |
| Butyl hydroxy toluene | 0.05 g |
| Iron oxides | 5 g |
| Talc | 30 g |
| Binding agent "SP5-1776" | 2 g |
| Mica-titanium | 3 g |
| Corn starch | 5 g |

| Example 14 - Anhydrous eyelid make-up | |
|---|---|
| Microcrystalline wax | 6 g |
| Petrolatum | 3 g |
| Japan wax | 2 g |
| Bees wax | 5 g |
| Propyl parahydroxybenzoate | 0.3 g |
| Wheat starch | 0.5 g |
| Binding agent "SP5-1776" | 2.5 g |
| Iron oxides | 5 g |
| Titanium dioxide | 1 g |
| Mica-titanium | 6 g |
| Isoparaffin, amount sufficient for | 100 g |

What is claimed is:
1. An anhydrous cosmetic make-up composition for application to the face, eyes or lips comprising
   (a) from 5 to 98 weight percent of a fatty body selected from the group consisting of an oil and a mixture of an oil and a wax, said oil comprising a member selected from the group consisting of paraffin oil, petrolatum oil, mineral oil having a boiling point between 310° and 410° C., Purcellin oil, perhydrosqualene, calophyllum oil, sweet almond oil, palm oil, avocado oil, olive oil, ricin oil, wheat germ oil, dimethylpolysiloxane, butyl myristate, isopropyl myristate, cetyl myristate, isopropyl palmitate, butyl stearate, hexadecyl stearate, isopropyl stearate, octyl stearate, isocetyl stearate, decyl oleate, hexyl laurate, propylene glycol dicaprylate, diisopropyl adipate, oleyl alcohol, linoleic alcohol, linolenic alcohol, isostearyl alcohol, octyl dodecanol, isopropyl lanolate, isocetyl lanolate, glycol octanoate, glycerol octanoate, glycol decanoate, glycerol decanoate and cetyl ricinoleate, said wax comprising a member selected from the group consisting of a microcrystalline wax, paraffin wax, petrolatum wax, ozokerite, montan wax, beeswax, spermaceti wax, lanolin wax, lanolin alcohols, hydrogenated lanolin, hydroxylated lanolin, acetylated lanolin, lanolin fatty acids, alcohol of acetylated lanolin, candellila wax, Carnauba wax, Japan wax cocoa butter, hydrogenated ricin oil, hydrogenated palm oil, hydrogenated tallow, hydrogenated coconut oil, polyethylene wax, propylene glycol monomyristate, myristyl myristate, silicone wax, cetyl alcohol, stearyl alcohol, mono-, di- and triglycerides solid at 25° C., stearyl monoethanolamide, rosin, glycol abietate, glycerol abietate, sucroglyceride, and the oleates, myristates, lanolates, stearates and dihydroxy stearates of calcium, magnesium, zinc and aluminum;

(b) from 0.5 to 40 weight percent of a mineral or organic charge selected from the group consisting of talc, rice starch, wheat starch, corn starch, oat or wheat germ powder and kaolin;

(c) from 0 to 80 weight percent of a solvent comprising a member selected from the group consisting of isoparaffins, linear or cyclic silicones having a boiling point lower than 200° C. and chlorinated solvents;

(d) from 0 to 30 weight percent of at least one colored pigment selected from the group consisting of black iron oxide, carbon black, chromium oxide, yellow iron oxide, brown iron oxide, red iron oxide, ultramarine, titanium dioxide, silver metallic powder, aluminum metallic powder, manganese pyrophosphate, ferric blue, carmine and organic lakes; and (e) from 0.5 to 20 weight percent, as a binding agent for components (a)–(d), above, a mixture of from 5 to 95 percent by weight of said mixture of finely divided silica having an average particle diameter of from 2 to about 10$\mu$ and about 95 to about 5 percent by weight of said mixture of finely divided polyethylene fibers having a fibrillar structure and having a specific area of 5 to 15m$^2$/g.

2. The cosmetic make-up composition of claim 1 wherein said colored pigment is present in an amount from 1 to 25 weight percent.

3. The cosmetic make-up composition of claim 1 wherein said mineral or organic charge is present in an amount from 1 to 30 weight percent.

4. The cosmetic make-up composition of claim 1 wherein said binding agent comprises a mixture of 50 to 60 percent by weight of said mixture of amorphous silica and from 40 to 50 percent by weight of said mixture of low density polyethylene having a specific area of 6 to 10m$^2$/g.

5. A cosmetic make-up composition in the form of a water-in-oil emulsion comprising:

(a) from 5 to 80 weight percent of a water phase;

(b) from 1 to 40 weight percent of an oil phase;

(c) from 0.5 to 40 weight percent of a mineral or organic charge selected from the group consisting of talc, rice starch, wheat starch, corn starch, oat or wheat germ powder and and kaolin.

(d) from 0 to 30 weight percent of at least one colored pigment selected from the group consisting of black iron oxide, carbon black, chromium oxide, yellow iron oxide, brown iron oxide, red iron oxide, ultramarine, titanium dioxide, silver metallic powder, aluminum metallic powder, manganese pyrophosphate, ferric blue, carmine and organic lakes; and (e) from 0.5 to 20 weight percent, as a binding agent for components (a)–(d), above, a mixture of from 5 to 95 percent by weight of said mixture of finely divided silica having an average particle diameter of from 2 to about 10$\mu$ and about 95 to about 5 percent by weight of said mixture of finely divided polyethylene fibers having a fibrillar structure and having a specific area of 5 to 15m$^2$/g.

6. The cosmetic make-up composition of claim 5 wherein said colored pigment is present in an amount from 1 to 25 weight percent.

7. The cosmetic make-up composition of claim 5 which also contains an emulsifying agent in an amount from 2 to 15 weight percent.

8. The cosmetic make-up composition of claim 5 wherein said binding agent comprises a mixture of 50 to 60 percent by weight of said mixture of amorphous silica and from 40 to 50 percent by weight of said mixture of low density polyethylene having a specific area of 6 to 10m$^2$/g.

9. A cosmetic make-up composition in the form of an oil-in-water emulsion comprising:

(a) from 1 to 30 weight percent of an oil phase;

(b) from 1 to 96.5 weight percent of a water phase;

(c) from 0.5 to 40 weight percent of a mineral or organic charge selected from the group consisting of talc, rice starch, wheat starch, corn starch, oat and wheat germ powder and kaolin;

(d) from 0 to 30 weight percent of at least one colored pigment selected from the group consisting of black iron oxide, carbon black, chromium oxide, yellow iron oxide, brown iron oxide, red iron oxide, ultramarine, titanium dioxide, silver metallic powder, aluminum metallic powder, manganese pyrophosphate, ferric blue, carmine and organic lakes; and (e) from 0.5 to 20 weight percent, as a binding agent for components (a)–(d), above, a mixture of from 5 to 95 percent by weight of said mixture of finely divided silica having an average particle diameter of from 2 to about 10$\mu$ and about 95 to 5 percent by weight of said mixture of finely divided polyethylene fibers having a fibrillar structure and having a specific area of 5 to 15m$^2$/g.

10. The cosmetic make-up composition of claim 9 wherein said colored pigement is present in an amount from 1 to 25 weight percent.

11. The cosmetic make-up composition of claim 9 which also contains an emulsifying agent in an amount from 1 to 15 weight percent.

12. The cosmetic make-up composition of claim 9 wherein said binding agent comprises a mixture of 50 to 60 percent by weight of said mixture of amorphous silica and from 40 to 50 percent by weight of said mixture of low density polyethylene having a specific area of 6 to 10m$^2$/g.

13. The cosmetic make-up composition of claim 9 wherein said colored pigment is admixed with a nacreous agent selected from the group consisting of bismuth oxychloride, mica-titanium and guanine crystals.

* * * * *